(12) United States Patent
Namiki

(10) Patent No.: US 10,488,647 B2
(45) Date of Patent: Nov. 26, 2019

(54) METHOD FOR MEASURING SCANNING PATTERN OF OPTICAL SCANNING APPARATUS, APPARATUS FOR MEASURING SCANNING PATTERN, AND METHOD FOR CALIBRATING IMAGE

(71) Applicant: OLYMPUS CORPORATION, Tokyo (JP)

(72) Inventor: Mitsuru Namiki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 44 days.

(21) Appl. No.: 15/708,269

(22) Filed: Sep. 19, 2017

(65) Prior Publication Data

US 2018/0003945 A1 Jan. 4, 2018

Related U.S. Application Data

(63) Continuation of application No. PCT/JP2015/001701, filed on Mar. 25, 2015.

(51) Int. Cl.
*G02B 23/24* (2006.01)
*G02B 23/26* (2006.01)
(Continued)

(52) U.S. Cl.
CPC ........ *G02B 23/2469* (2013.01); *G01B 11/002* (2013.01); *G02B 23/26* (2013.01); *G06T 5/001* (2013.01); *G06T 2207/10068* (2013.01)

(58) Field of Classification Search
None
See application file for complete search history.

(56) References Cited

U.S. PATENT DOCUMENTS

2005/0203343 A1* 9/2005 Kang ................. A61B 1/00009
600/160
2006/0072843 A1 4/2006 Johnston
(Continued)

FOREIGN PATENT DOCUMENTS

JP 5190267 B2 4/2013
JP 2014-018556 A 2/2014
(Continued)

OTHER PUBLICATIONS

International Preliminary Report on Patentability together with the Written Opinion from related International Applicatio No. PCT/JP2015/001701 dated Oct. 5, 2017.
(Continued)

*Primary Examiner* — Fernando Alcon
(74) *Attorney, Agent, or Firm* — Scully, Scott, Murphy & Presser, P.C.

(57) ABSTRACT

An apparatus for measuring a scanning pattern of an optical scanning apparatus can easily reduce the effect of stray light and improve the measurement accuracy of the scanning pattern. An apparatus for measuring a scanning pattern of an optical scanning apparatus (100), which scans an object being illuminated with illumination light and generates a display image of the object being illuminated, includes a screen (11) scanned by the illumination light and an optical position detector (12) that detects the position of an irradiation spot of the illumination light on the screen (11). The apparatus for measuring a scanning pattern sequentially detects a position of the irradiation spot at predetermined time points with the optical position detector (12) during scanning of the screen (11) to measure the scanning pattern of the illumination light.

5 Claims, 7 Drawing Sheets

(51) Int. Cl.
*G01B 11/00* (2006.01)
*G06T 5/00* (2006.01)
*G02B 26/10* (2006.01)
*A61B 1/00* (2006.01)

(56) References Cited

U.S. PATENT DOCUMENTS

2009/0316116 A1* 12/2009 Melville .............. A61B 1/0008
   353/31
2018/0080766 A1* 3/2018 Johnson .................. G01S 17/02

FOREIGN PATENT DOCUMENTS

| JP | 2014-090780 A | 5/2014 | | |
|---|---|---|---|---|
| JP | 2015-020002 A | 2/2015 | | |
| WO | WO-2013094569 A1 * | 6/2013 | ........... | A61B 1/0653 |
| WO | WO-2014017065 A1 * | 1/2014 | ......... | A61B 1/00057 |

OTHER PUBLICATIONS

International Search Report dated Jun. 16, 2015 issued in PCT/JP2015/001701.
Japanese Office Action dated Mar. 12, 2019 in Japanese Patent Application No. 2017-507111.
Chinese Office Action dated Jun. 3, 2019 in Chinese Patent Application No. 201580077863.1.
Decision of Refusal dated Sep. 10, 2019 in Japanese Patent Application No. 2017-507111.

* cited by examiner

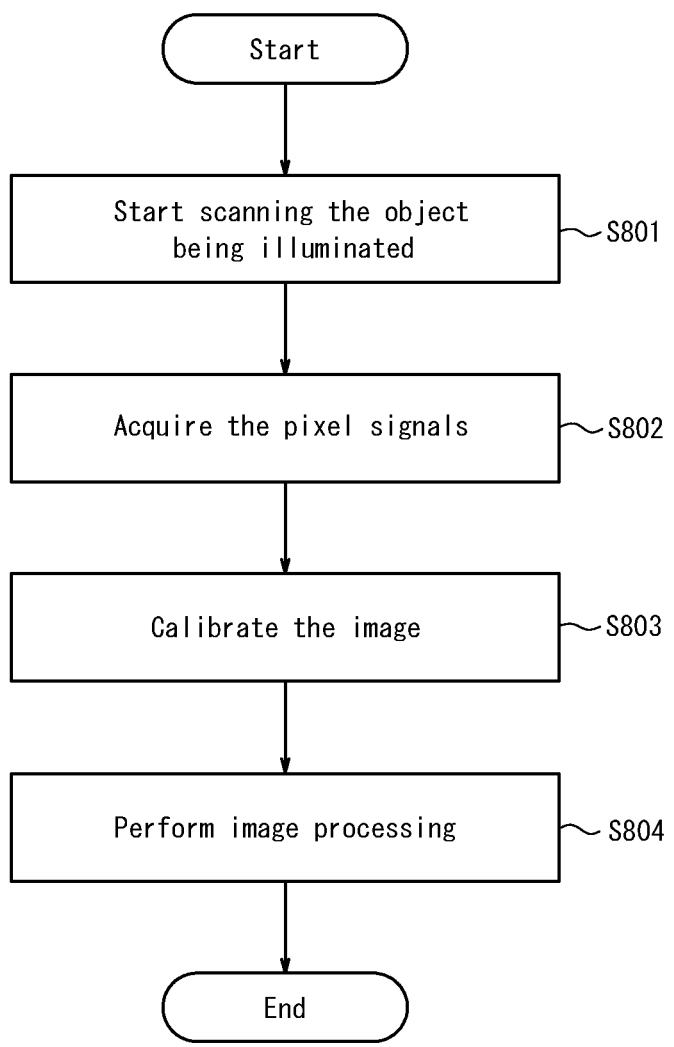

METHOD FOR MEASURING SCANNING PATTERN OF OPTICAL SCANNING APPARATUS, APPARATUS FOR MEASURING SCANNING PATTERN, AND METHOD FOR CALIBRATING IMAGE

CROSS-REFERENCE TO RELATED APPLICATION

The present application is a Continuing Application based on International Application PCT/JP2015/001701 filed on Mar. 25, 2015, the content of which is incorporated herein by reference.

TECHNICAL FIELD

This disclosure relates to a method for measuring a scanning pattern of an optical scanning apparatus, an apparatus for measuring a scanning pattern, and a method for calibrating an image.

BACKGROUND

A known example of an optical scanning apparatus scans an object being illuminated by irradiating the object being illuminated with illumination light from an optical fiber through an illumination optical system. The scanning endoscope apparatus scans while displacing the emission end of the optical fiber with an actuator and deflecting the illumination light, detects backscattered light from the object being illuminated, and generates an image (for example, see JP 5190267 B2 (PTL 1)).

Before scanning a target area of the object being illuminated, the optical scanning apparatus disclosed in PTL 1 directly scans an optical position detector provided with a coordinate information acquisition function, such as a Position Sensitive Detector (PSD), with illumination light and acquires the scanning pattern of the illumination light. During scanning of a target area of the object being illuminated, the optical scanning apparatus uses the scanning pattern, acquired in advance, to calibrate the pixel positions in the image of the object being illuminated obtained by scanning the object being illuminated and generates a display image.

CITATION LIST

Patent Literature

PTL 1: JP 5190267 B2

SUMMARY

One aspect of this disclosure is directed to a method for measuring a scanning pattern of an optical scanning apparatus that scans an object being illuminated with illumination light and generates a display image of the object being illuminated, the method comprising:
  scanning a screen with the illumination light; and
  acquiring irradiation position information by sequentially detecting, with an optical position detector, a position of an irradiation spot of the illumination light on the screen at a predetermined plurality of time points during scanning of the screen.

Another aspect of this disclosure is directed to an apparatus for measuring a scanning pattern of an optical scanning apparatus that scans an object being illuminated with illumination light and generates a display image of the object being illuminated, the apparatus for measuring a scanning pattern comprising:
  a screen scanned by the illumination light; and
  an optical position detector configured to detect a position of an irradiation spot of the illumination light on the screen, wherein
  the apparatus for measuring a scanning pattern sequentially detects the position of the irradiation spot at a predetermined plurality of time points with the optical position detector during scanning of the screen to measure the scanning pattern of the illumination light.

The screen may have a thickness equal to or less than a diameter of the irradiation spot.

The apparatus for measuring a scanning pattern of an optical scanning apparatus may further comprise a projection optical system configured to project the irradiation spot on the screen onto the optical position detector.

When the apparatus comprises the projection optical system, at least one of a first condition, a second condition, and a third condition is preferably satisfied,
  the first condition being that the screen has a thickness equal to or less than a diameter of the irradiation spot,
  the second condition being that a diffusion angle of the illumination light by the screen is equal to or greater than a scanning angle of view, and
  the third condition being that a numerical aperture of the projection optical system on the screen side is 0.2 or greater.

The apparatus for measuring a scanning pattern of an optical scanning apparatus may further comprise a storage configured to store the measured scanning pattern of the illumination light.

The apparatus for measuring a scanning pattern of an optical scanning apparatus may further comprise an image acquisition unit configured to image the screen and acquire an image of the scanning pattern of the illumination light.

Another aspect of this disclosure is directed to a method for calibrating an image in an optical scanning apparatus that calibrates pixel positions of an image of an object being illuminated, the pixel positions being obtained by scanning the object being illuminated with illumination light, and generates a display image of the object being illuminated, the method comprising:
  acquiring a scanning pattern of the illumination light before scanning of the object being illuminated; and
  generating the display image by calibrating pixel positions of the image of the object being illuminated based on the scanning pattern acquired in the step of acquiring a scanning pattern, the pixel positions being obtained by scanning the object being illuminated, wherein
  the step of acquiring a scanning pattern comprises
    scanning a screen with the illumination light; and
    acquiring irradiation position information by sequentially detecting, with an optical position detector, a position of an irradiation spot of the illumination light on the screen at a predetermined plurality of time points during scanning of the screen.

The step of generating the display image may comprise:
  acquiring pixel signals of the object being illuminated at a predetermined plurality of time points during scanning of the object being illuminated; and
  arranging the pixel signals acquired in the step of acquiring pixel signals at pixel positions corresponding to the irradiation position information at the same time points as in the step of acquiring irradiation position information.

BRIEF DESCRIPTION OF THE DRAWINGS

In the accompanying drawings:

FIG. 8 is a flowchart illustrating the main processing of image calibration operations by the endoscopic observation apparatus in FIG. 7.

DETAILED DESCRIPTION

If the optical scanning apparatus is, for example, a scanning endoscope, a large angle of view is required, such as 90°. In this case, the illumination light emitted from the scanning endoscope rapidly increases a distance from the optical axis of the illumination optical system at the scanning tip. On the other hand, the size of the light receiving surface of a PSD, for example, is at most about 10 mm square. Directly measuring the scanning pattern of illumination light with a PSD, therefore, requires that the light receiving surface of the PSD be placed within approximately 5 mm from the emission end face of the scanning endoscope.

Disposing the PSD near the emission end face of the scanning endoscope, however, gives rise to stray light due to multiple reflections between the PSD and the emission end face in a state of high energy density. Such stray light causes the detection accuracy of the irradiation position of illumination light to decrease. Consequently, the measurement accuracy of the scanning pattern decreases with the calibration method disclosed in PTL 1, leading to concerns over a decrease in image quality of the display image.

One possible method for decreasing such stray light is to dispose an optical element, such as a wave plate or a polarizer, in front of the PSD. However, the PSD is provided with a cover glass or the like to protect the light receiving surface, which further reduces the distance between the emission end face of the scanning endoscope and the PSD, and that makes it difficult to dispose an optical element. Furthermore, an optical element such as a wave plate or a polarizer exhibits incidence angle dependence. Therefore, the ideal characteristics with respect to incident light cannot be obtained near an angle of view of 90° (an angle of incidence of 45°), and a reduction in the position detection accuracy is inevitable. This problem similarly occurs in other apparatuses, such a laser scanning microscope that scans a sample through an objective lens by deflecting laser light.

In light of these considerations, it would be helpful to provide a method for measuring a scanning pattern of an optical scanning apparatus, an apparatus for measuring a scanning pattern, and a method for calibrating an image that can easily reduce the effect of stray light, improve the measurement accuracy of the scanning pattern, and achieve highly accurate image calibration.

Embodiments of this disclosure are described below with reference to the drawings.

Embodiment 1

Figure 1:
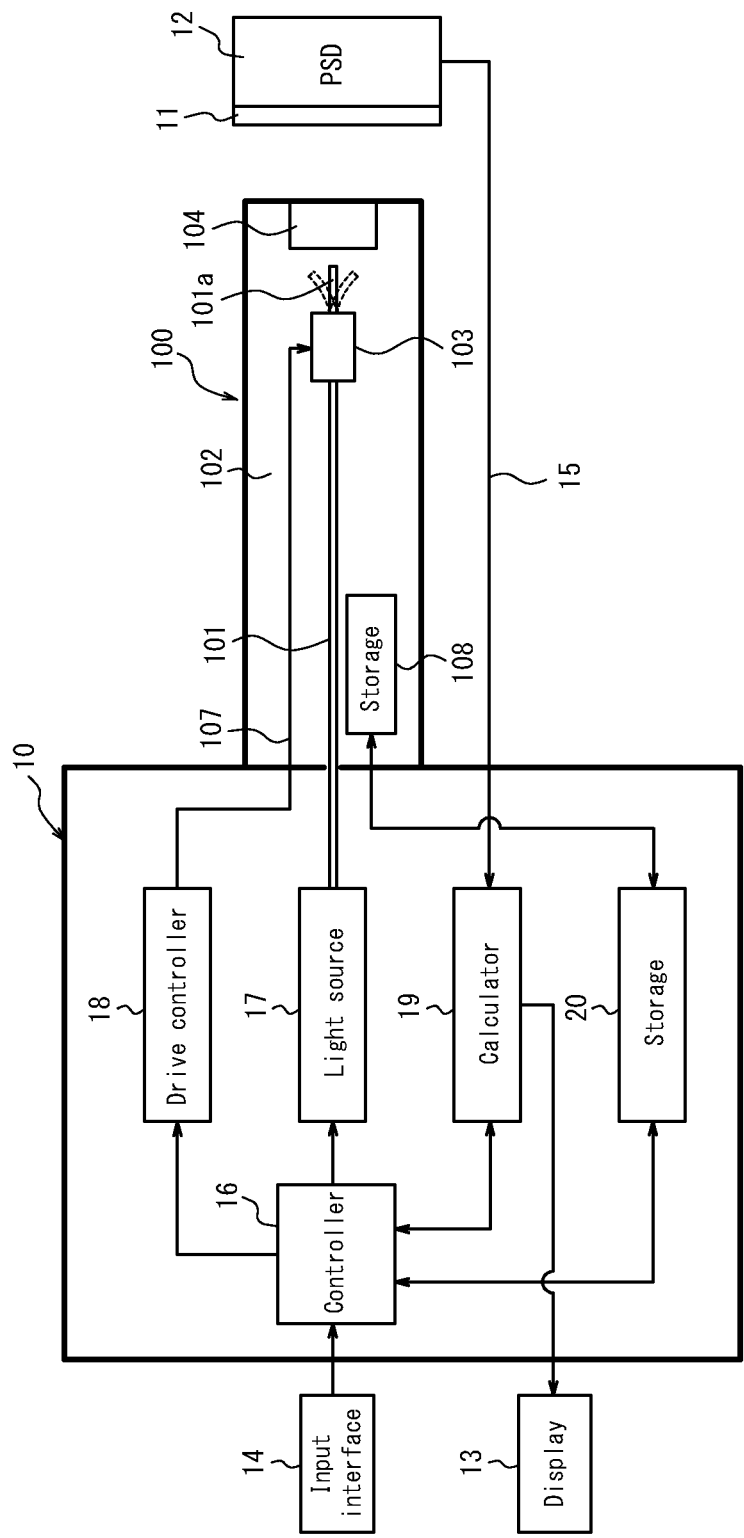
FIG. 1 is a block diagram illustrating the main configuration of an apparatus for measuring a scanning pattern according to Embodiment 1.

FIG. 1 is a block diagram illustrating the main configuration of an apparatus for measuring a scanning pattern according to Embodiment 1. The apparatus for measuring a scanning pattern according to this embodiment is for measuring the scanning pattern of a scanning endoscope (scope) 100, mainly at the time of product shipment. The apparatus for measuring a scanning pattern includes a measurement apparatus body 10, a screen 11, and a PSD 12. As necessary, the measurement apparatus body 10 includes a display 13 and an input interface 14, such as a keyboard, a mouse, or a touch panel.

The scanning endoscope 100 is detachably connected to the measurement apparatus body 10 by a connector or the like. The screen 11 is mounted directly on the light receiving surface of the PSD 12 and is disposed at the position scanned by illumination light emitted from the scanning endoscope 100. The screen 11 is preferably disposed at the position of the object being observed (object being illuminated) at the time of endoscopic observation using the scanning endoscope 100. The screen 11 also preferably has a thickness equal to or less than the spot diameter of the irradiated illumination light.

The PSD 12 outputs a detection signal corresponding to the irradiation position of illumination light that passes through the screen 11 and is incident on the light receiving surface. The detection signal output from the PSD 12 is input into the measurement apparatus body 10 through a signal wire 15.

An optical fiber 101 for illumination and optical fibers 102 for receiving light (see FIG. 2) are disposed inside the scanning endoscope 100 and extend from the base end joined to the measurement apparatus body 10 to the insertion tip. Illumination light from the measurement apparatus body 10 can enter the optical fiber 101 for illumination while the scanning endoscope 100 is connected to the measurement apparatus body 10.

Figure 2:
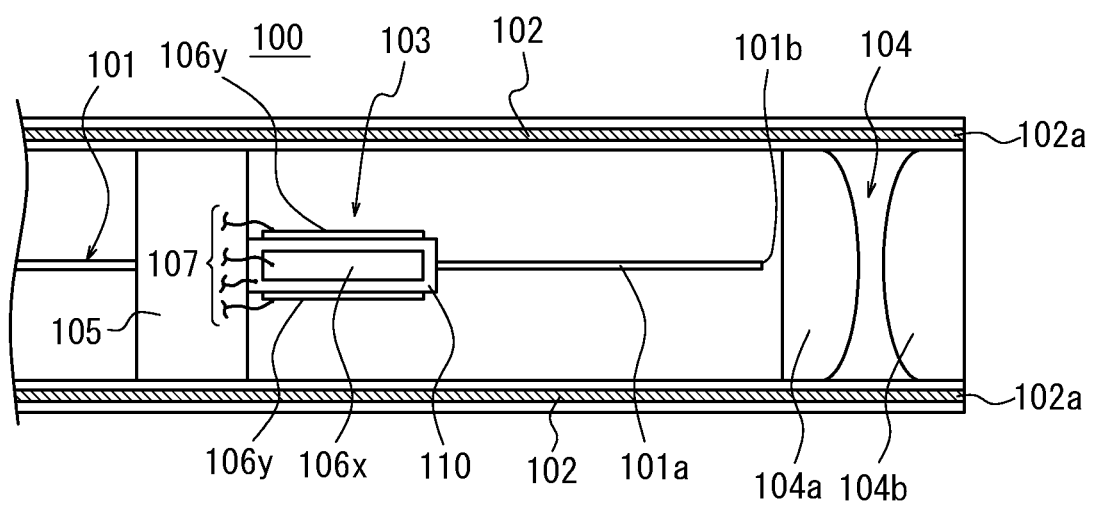
FIG. 2 is a partially expanded cross-sectional diagram of the insertion tip of the optical scanning endoscope in FIG. 1.

As illustrated in the partially expanded cross-sectional diagram of FIG. 2, an actuator 103 and an illumination optical system 104 are mounted in the insertion tip of the scanning endoscope 100. The actuator 103 includes a ferrule 110 as a fiber holder that holds an emission end 101a of the optical fiber 101 for illumination by the emission end 101a passing through the ferrule 110. The optical fiber 101 for illumination is adhered to the ferrule 110. The end of the ferrule 110 opposite from an emission end face 101b of the optical fiber 101 for illumination is joined to a support 105 so that the ferrule 110 is supported at one end by the support 105 to allow oscillation. The optical fiber 101 for illumination extends through the support 105.

The ferrule 110 is, for example, made of a metal such as nickel. The ferrule 110 may be formed in any shape, such as a quadrangular prism or a cylinder. Piezoelectric elements 106x and 106y are mounted on the ferrule 110 to oppose each other in the x-direction and the y-direction, where the x-direction and y-direction are orthogonal to each other in a plane orthogonal to the z-direction, and the z-direction is a direction parallel to the optical axis direction of the optical fiber 101 for illumination. Only one of the piezoelectric elements 106x is illustrated in FIG. 2. The piezoelectric elements 106x and 106y are rectangular, with the long sides in the z-direction. The piezoelectric elements 106x and 106y each have an electrode formed on both surfaces in the thickness direction and are each configured to be capable of expanding and contracting in the z-direction upon voltage being applied in the thickness direction via the opposing electrodes.

Corresponding wiring cables 107 are connected to the electrode surfaces of the piezoelectric elements 106x and 106y opposite the electrode surfaces adhered to the ferrule 110. Similarly, corresponding wiring cables 107 are connected to the ferrule 110, which acts as a common electrode for the piezoelectric elements 106x and 106y. To the two piezoelectric elements 106x opposite each other in the x-direction, in-phase AC voltage is applied from the measurement apparatus body 10 through the corresponding wiring cables 107. Similarly, to the two piezoelectric elements 106y opposite each other in the y-direction, in-phase AC voltage is applied from the measurement apparatus body 10 through the corresponding wiring cables 107.

With this configuration, when one of the two piezoelectric elements 106x expands, the other contracts, causing the ferrule 110 to vibrate by bending in the x-direction. Similarly, when one of the two piezoelectric elements 106y expands, the other contracts, causing the ferrule 110 to vibrate by bending in the y-direction. As a result, the x-direction vibration and y-direction vibration are combined, so that the ferrule 110 is deflected integrally with the emission end 101a of the optical fiber 101 for illumination. Accordingly, upon illumination light entering the optical fiber 101 for illumination from the measurement apparatus body 10, the illumination light emitted from the emission end face 101b is deflected in two dimensions.

The optical fibers 102 for receiving light are disposed as a bundle at the outer circumferential portion of the scanning endoscope 100. A non-illustrated detection lens may also be disposed at the entrance tip 102a side of the optical fibers 102 for receiving light. While the scanning endoscope 100 is connected to the observation apparatus body for endoscopic observation, reflected light, fluorescent light, or other light is yielded by the object being observed (object being illuminated) as a result of irradiation with the illumination light from the optical fiber 101 for illumination. The optical fibers 102 for receiving light capture this light as signal light and guide the signal light to the observation apparatus body.

The example of the illumination optical system 104 in FIG. 2 is configured by two projection lenses 104a, 104b. The projection lenses 104a, 104b are configured so as to concentrate illumination light, emitted from the emission end face 101b of the optical fiber 101 for illumination, on a predetermined focal position. The illumination optical system 104 is not limited to two projection lenses 104a, 104b and may be configured as a single lens or as three or more lenses.

As illustrated in FIG. 1, the scanning endoscope 100 further includes a storage 108. Scanning pattern information on the illumination light from the optical fiber 101 for illumination when the actuator 103 of the scanning endoscope 100 is driven with a predetermined drive signal is stored in the storage 108. During endoscopic observation using the scanning endoscope 100, the scanning pattern information stored in the storage 108 is read by the observation apparatus body while the scanning endoscope 100 is connected to the observation apparatus body.

The measurement apparatus body 10 in FIG. 1 includes a controller 16 that controls operations of the apparatus overall, a light source 17, a drive controller 18, a calculator 19, and a storage 20.

The light source 17 includes a light source such as a laser diode or a Diode-Pumped Solid-State (DPSS) laser. As during endoscopic observation of color images with the scanning endoscope 100, the light source 17 may be configured with a plurality of lasers that emit blue, green, and red laser light, or the light source 17 may be configured with a single laser for scanning pattern measurement. Light emitted from the light source 17 is incident on the optical fiber 101 for illumination of the scanning endoscope 100.

The drive controller 18 supplies the actuator 103 of the scanning endoscope 100 with a predetermined drive signal, over the wiring cables 107, that is similar to the drive signal for scanning the target area of the object being observed during endoscopic observation, and vibrates the emission end 101a of the optical fiber 101 for illumination. In this embodiment, the actuator 103 includes the piezoelectric elements 106x and 106y. As drive signals, the drive controller 18 thus applies voltage that gradually increases and then decreases in amplitude to the piezoelectric elements 106x and 106y. The drive signals differ in phase by nearly 90° and are at or near the resonance frequency of the vibrated portion, which for example includes the emission end 101a of the optical fiber 101 for illumination. As a result, the emission end face 101b of the optical fiber 101 for illumination is displaced in a spiral shape centered on the optical axis of the illumination optical system 104, and the screen 11 is scanned in a spiral shape by the illumination light emitted from the emission end face 101b.

The calculator 19 receives input of the detection signal output by the PSD 12 and converts the detection signal into coordinates (x, y) at a sequential predetermined plurality of time points $t_k$ (k=0, 1, . . . , n) from the start of scanning of the screen 11 by the illumination light. As a result, the calculator 19 captures the position of the irradiation spot on the screen 11 at sequential predetermined time points from the start of scanning of the screen 11 by the illumination light. The calculator 19 may smooth the error in the coordinate position of the illumination spot as necessary using a method such as polynomial approximation. The result of calculation by the calculator 19, i.e. the irradiation position information associated with the elapsed time of the scan, is stored in the storage 20. Upon the irradiation position information over one scan being stored in the storage 20, the controller 16 stores the irradiation position information as scanning pattern information in the storage 108 of the scanning endoscope 100.

The storage 20 stores information such as control programs of the measurement apparatus body 10. The storage 20 also functions as a working memory of the calculator 19, as described above. The storage 20 may be an internal memory of the measurement apparatus body 10 or may be a portable storage medium (such as a memory card) removable from the measurement apparatus body 10.

Figure 3:
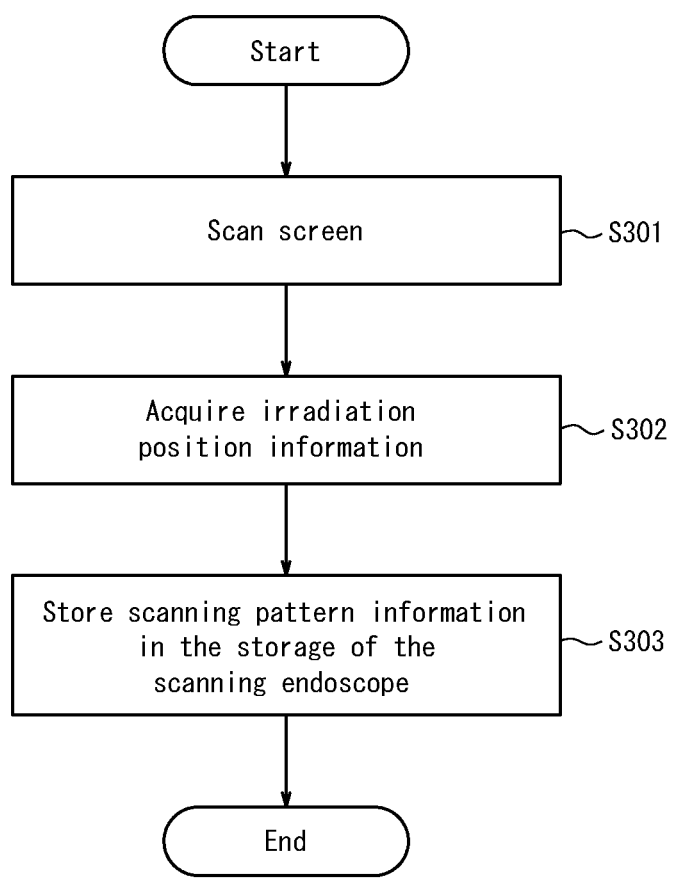
FIG. 3 is a flowchart illustrating the main processing for scanning pattern measurement by the apparatus for measuring a scanning pattern in FIG. 1.

FIG. 3 is a flowchart illustrating the main processing for scanning pattern measurement of the scanning endoscope 100 by the apparatus for measuring a scanning pattern according to this embodiment. To prepare for measurement, the scanning endoscope 100 to be measured is connected to the measurement apparatus body 10, and the PSD 12 with the screen 11 mounted thereon is disposed facing the emission end of the scanning endoscope 100. In this state, the controller 16 drives the light source 17, and the drive controller 18 drives the actuator 103 of the scanning endoscope 100 to start scanning of the screen 11 with illumination light (step S301).

Next, during scanning of the screen 11, the controller 16 uses the calculator 19 to convert the detection signal input from the PSD 12 into coordinates (x, y) at a sequential predetermined plurality of time points $t_k$ (k=0, 1, . . . , n) from the start to the end of scanning. By doing so, the controller 16 captures the sequential position of the irradiation spot on the screen 11 with the calculator 19, thereby acquiring the irradiation position information (step S302). This irradiation position information is associated with the elapsed time of the scan and stored in the storage 20.

Subsequently, upon the irradiation position information over one scan being stored in the storage 20, the controller 16 ends the scanning of the screen 11, stores the irradiation position information over one scan, which was stored in the storage 20, in the storage 108 of the scanning endoscope 100 as scanning pattern information (step S303), and ends the scanning pattern measurement operation of the scanning endoscope 100.

In the flowchart illustrated in FIG. 3, step S301 corresponds to a step of scanning a screen, and step S302 corresponds to a step of acquiring irradiation position information. Processing that includes steps S301 to S303 corresponds to a step of acquiring a scanning pattern.

The apparatus for measuring a scanning pattern according to this embodiment uses illumination light irradiated from the scanning endoscope 100 to be measured in order to scan the screen 11, which is mounted directly on the light receiving surface of the PSD 12. The illumination light incident on the screen 11 is then scattered by the screen 11, and a portion of the scattered light passing through the screen 11 is incident on the light receiving surface of the PSD 12.

Among the light scattered by the screen 11, light that returns in the direction of the scanning endoscope 100 (backscattered light) is highly scattered. A portion of this scattered light is reflected by the scanning endoscope 100 and is incident again on the screen 11. The light that is incident again on the screen 11 is then scattered once again by the screen 11. Hence, the light that passes through the screen 11 to be incident on the PSD 12 is extremely weak. The effect of stray light incident on the PSD 12 because of multiple reflections between the screen 11 and the scanning endoscope 100 can therefore easily be reduced, allowing improvement in the measurement accuracy of the scanning pattern. Furthermore, by setting the thickness of the screen 11 to be equal to or less than the diameter of the irradiation spot of illumination light incident on the screen 11, the extent to which the irradiation spot incident on the PSD 12 is blurred can be reduced, thereby further improving the scanning pattern measurement accuracy.

Embodiment 2

Figure 4:
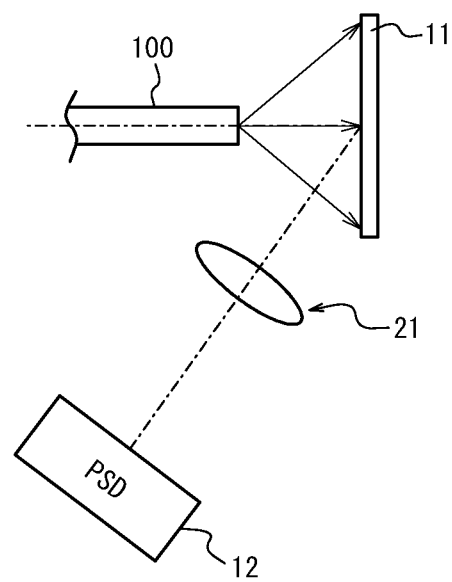
FIG. 4 illustrates the main configuration of an apparatus for measuring a scanning pattern according to Embodiment 2.

FIG. 4 illustrates the main configuration of an apparatus for measuring a scanning pattern according to Embodiment 2. The apparatus for measuring a scanning pattern according to this embodiment differs from the scanning pattern measurement apparatus in FIG. 1 in the arrangement of the PSD 12. FIG. 4 illustrates only the portion of the configuration that differs from FIG. 1. The differences in configuration from FIG. 1 are described below.

As is clear from FIG. 4, the apparatus for measuring a scanning pattern according to this embodiment causes a portion of the backscattered light occurring at the screen 11 to be incident on the PSD 12 through a projection optical system 21. The light receiving surface of the PSD 12 is disposed at a position conjugate with the screen 11 with respect to the projection optical system 21. As a result, the projection optical system 21 projects the irradiation spot of illumination light incident on the screen 11 onto the light receiving surface of the PSD 12, allowing measurement of the scanning pattern of the illumination light. In this embodiment, the screen 11 is preferably configured so that the diffusion angle of the illumination light is equal to or greater than the scanning angle of view. The projection optical system 21 is preferably configured to have a numerical aperture on the screen 11 side of 0.2 or greater.

In this way, the projection optical system 21 projects the irradiation spot on the screen 11 onto the PSD 12 with backscattered light from the screen 11, allowing measurement of the scanning pattern of the illumination light in this embodiment. Among the light scattered at the screen 11, the backscattered light is highly scattered. A portion of this scattered light is reflected by the scanning endoscope 100 and is incident again on the screen 11. The light that is incident again on the screen 11 is then scattered once again by the screen 11. Hence, even if a portion of that backscattered light is incident on the PSD 12 through the projection optical system 21, the light is extremely weak. As in Embodiment 1, the effect of stray light incident on the PSD 12 because of multiple reflections between the screen 11 and the scanning endoscope 100 can therefore easily be reduced, allowing improvement in the measurement accuracy of the scanning pattern.

As in Embodiment 1, by setting the thickness of the screen 11 to be equal to or less than the diameter of the irradiation spot of illumination light incident on the screen 11, the extent to which the irradiation spot incident on the PSD 12 is blurred can be reduced in this embodiment as well, thereby further improving the scanning pattern measurement accuracy. Also, by setting the diffusion angle of the illumination light by the screen 11 to be equal to or greater than the scanning angle of view, the proportion of the backscattered light that is collected by the projection optical system 21 can be increased. The amount of light incident on the PSD 12 can therefore be increased, further improving the scanning pattern measurement accuracy. Similarly, by setting the numerical aperture of the projection optical system 21 on the screen 11 side to be 0.2 or greater, a greater amount of backscattered light can be collected, allowing an increase in the amount of light incident on the PSD 12 and further improving the scanning pattern measurement accuracy.

Embodiment 3

Figure 5:
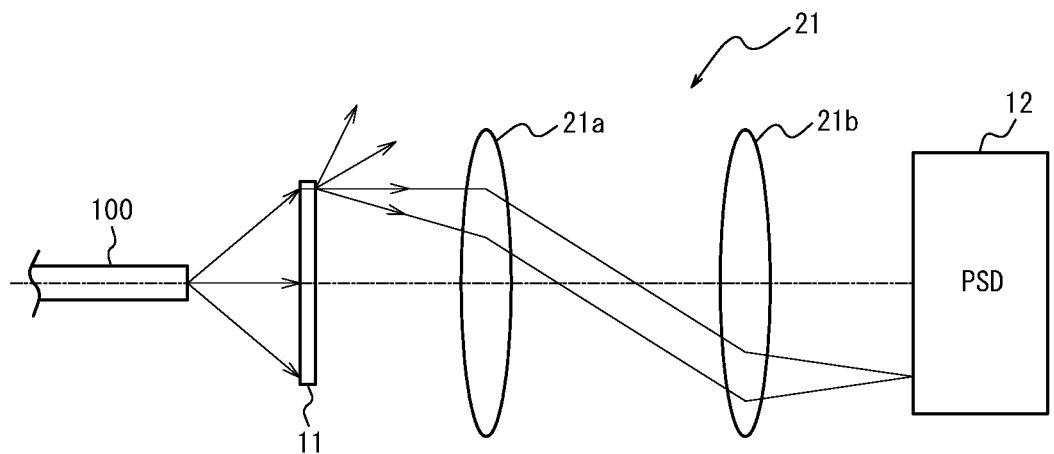
FIG. 5 illustrates the main configuration of an apparatus for measuring a scanning pattern according to Embodiment 3.

FIG. 5 illustrates the main configuration of an apparatus for measuring a scanning pattern according to Embodiment 3. The apparatus for measuring a scanning pattern according to this embodiment differs from the apparatus for measuring a scanning pattern in FIG. 4 in the arrangement of the PSD 12. FIG. 5 illustrates only the portion of the configuration that differs from FIG. 4. The differences in configuration from FIG. 4 are described below.

As is clear from FIG. 5, the apparatus for measuring a scanning pattern according to this embodiment causes a portion of the forward-scattered light occurring at the screen 11 to be incident on the PSD 12 through a projection optical system 21. The projection optical system 21 for example includes two relay lenses 21a and 21b. The light receiving surface of the PSD 12 is disposed at a position conjugate with the screen 11 with respect to the projection optical system 21. As a result, the projection optical system 21 projects the irradiation spot of illumination light incident on the screen 11 onto the light receiving surface of the PSD 12, allowing measurement of the scanning pattern of the illumination light.

In this way, the projection optical system 21 projects the irradiation spot on the screen 11 onto the PSD 12 with forward-scattered light from the screen 11, allowing measurement of the scanning pattern of the illumination light in this embodiment. Among the light scattered at the screen 11, the backscattered light is highly scattered. A portion of this scattered light is reflected by the scanning endoscope 100 and is incident again on the screen 11. The light that is incident again on the screen 11 is then scattered once again by the screen 11. Hence, even if a portion of the forward-scattered light is incident on the PSD 12 through the projection optical system 21, the light is extremely weak. As in Embodiment 1, the effect of stray light incident on the PSD 12 because of multiple reflections between the screen 11 and the scanning endoscope 100 can therefore easily be reduced, allowing improvement in the measurement accuracy of the scanning pattern.

In this embodiment as well, as in Embodiment 2, satisfying at least one of the following conditions further improves the scanning pattern measurement accuracy. Condition 1: the thickness of the screen 11 is set to be equal to or less than the diameter of the irradiation spot of illumination light incident on the screen 11. Condition 2: the diffusion angle of the illumination light by the screen 11 is set to be equal to or greater than the scanning angle of view. Condition 3: the numerical aperture of the projection optical system 21 on the screen 11 side is set to be 0.2 or greater.

Embodiment 4

Figure 6:
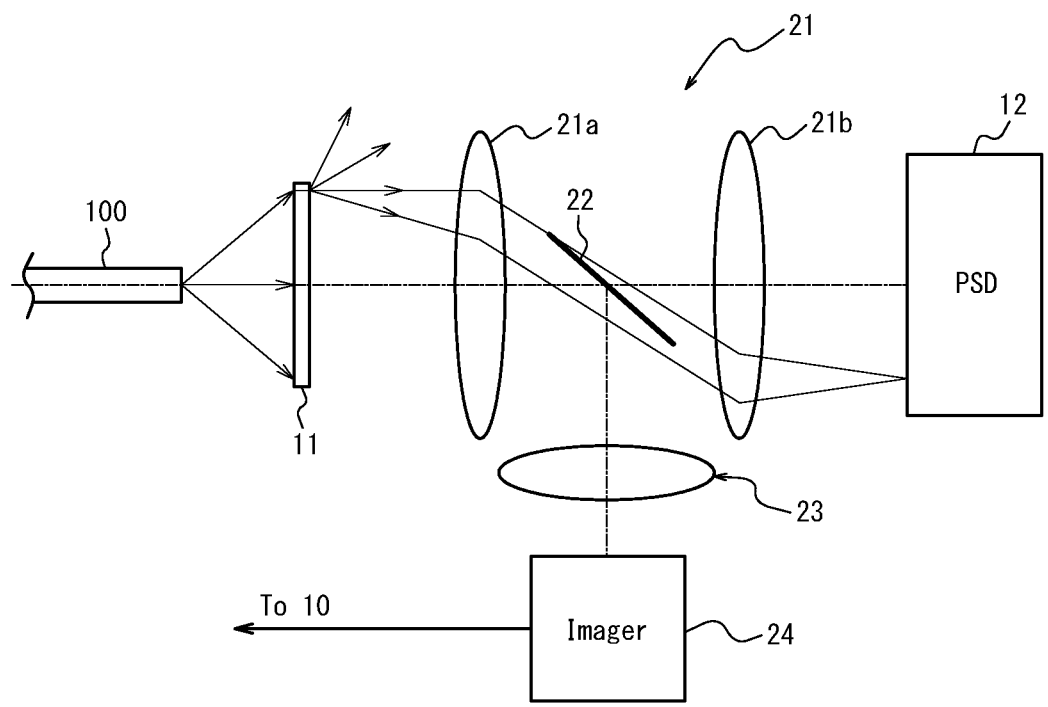
FIG. 6 illustrates the main configuration of an apparatus for measuring a scanning pattern according to Embodiment 4.

FIG. 6 illustrates the main configuration of an apparatus for measuring a scanning pattern according to Embodiment 4. The apparatus for measuring a scanning pattern according to Embodiment 4 has the configuration of the apparatus for measuring a scanning pattern illustrated in FIG. 5, with the addition of a beam splitter 22, an image forming optical system 23, and an imager 24. FIG. 6 illustrates only the portion of the configuration that differs from FIG. 5. The differences in configuration from FIG. 5 are described below.

The beam splitter 22 is, for example, composed of a half-mirror placed on the optical axis between the two relay lenses 21a and 21b constituting the projection optical system 21. The beam splitter 22 reflects a portion of the light traveling towards the relay lens 21b. The image forming optical system 23 forms an image on the imager 24 with light reflected by the beam splitter 22. The imager 24 is configured to include a CCD or other such device, the output of which for example is subjected to image processing by the measurement apparatus body 10 in FIG. 1 and is displayed on the display 13.

This embodiment not only achieves the effects of Embodiment 3 but also allows the scanning pattern of the scanning endoscope 100 to be observed as an image. A good judgement of the scanning pattern can thus, for example, be made visually.

Next, an embodiment of an endoscopic observation apparatus that uses the scanning endoscope 100 for which the scanning pattern has been measured as described in Embodiments 1 to 4 is described.

Embodiment 5

Figure 7:
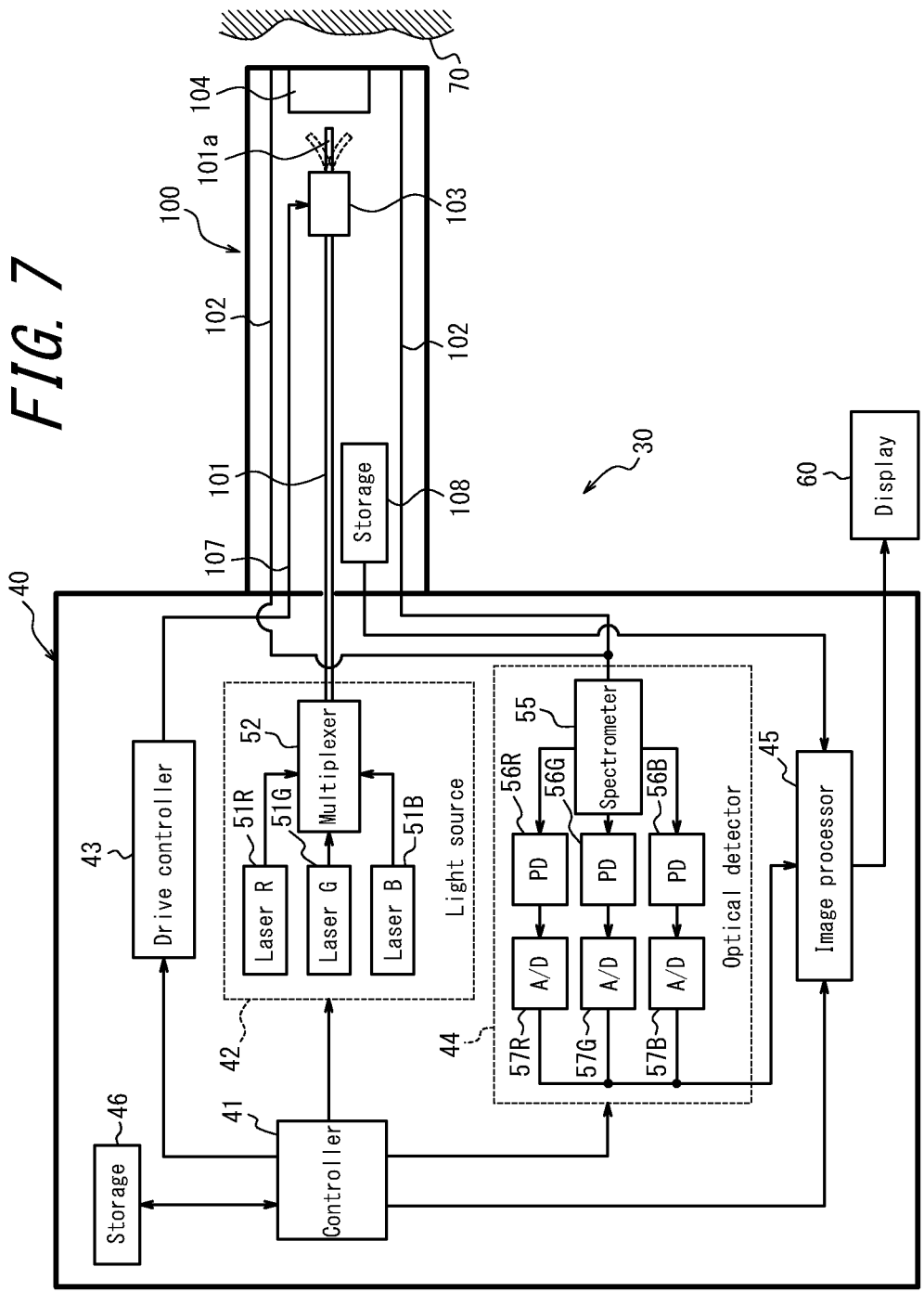
FIG. 7 is a block diagram schematically illustrating the main configuration of an endoscopic observation apparatus according to Embodiment 5.

FIG. 7 is a block diagram schematically illustrating the main configuration of an endoscopic observation apparatus according to Embodiment 5. An endoscopic observation apparatus 30 illustrated in FIG. 7 includes an observation apparatus body 40, a display 60, and a scanning endoscope 100.

The scanning endoscope 100 is detachably connected to the observation apparatus body 40 by a connector or the like.

The observation apparatus body 40 includes a controller 41 that controls the entire endoscopic observation apparatus 30, a light source 42, a drive controller 43, an optical detector 44, an image processor 45, and a storage 46.

The light source 42 includes lasers 51R, 51G, 51B and a multiplexer 52. The laser 51R emits red laser light, the laser 51G emits green laser light, and the laser 51B emits blue laser light. For example, Diode-Pumped Solid-State (DPSS) lasers or laser diodes may be used as the lasers 51R, 51G, and 51B. The wavelength of each color of light may, for example, be from 440 nm to 460 nm for blue, 515 nm to 532 nm for green, and 635 nm to 638 nm for red. The laser light emitted from the lasers 51R, 51G, and 51B is combined on the same axis by the multiplexer 52 and is incident on the optical fiber 101 for illumination of the scanning endoscope 100. The light source 42 may include a different plurality of light sources. The light source 42 may also be stored in a housing that is separate from the observation apparatus body 40 and is connected to the observation apparatus body 40 by a signal wire. In this case, the optical fiber 101 for illumination of the scanning endoscope 100 is detachably connected to the housing that includes the light source 42.

The drive controller 43 supplies the actuator 103 of the scanning endoscope 100 with a required drive signal, over the wiring cables 107, for scanning the target area of the object being observed 70 and vibrates the emission end 101a of the optical fiber 101 for illumination. The required drive signal is the same drive signal as when measuring the scanning pattern of the scanning endoscope 100. For example, as drive signals, the drive controller 43 applies voltage that gradually increases and then decreases in amplitude to the piezoelectric elements 106x and 106y. The drive signals differ in phase by nearly 90° and are at or near the resonance frequency of the vibrated portion, which includes the emission end 101a of the optical fiber 101 for illumination. As a result, the emission end face 101b of the optical fiber 101 for illumination is displaced in a spiral shape centered on the optical axis of the illumination optical system 104, and the target area of the object being observed 70 is scanned in a spiral shape by the illumination light emitted from the emission end face 101b.

The optical detector 44 includes a spectrometer 55, photodetectors (PDs) 56R, 56G, 56B, and Analog-Digital Converters (ADCs) 57R, 57G, 57B. While the scanning endoscope 100 is connected to the observation apparatus body 40, the spectrometer 55 is connected to the optical fibers 102 for receiving light of the scanning endoscope 100. The signal light guided by the optical fibers 102 for receiving light is divided for example into the colors R, G, B. The PDs 56R, 56G, 56B detect the light of the corresponding color split by the spectrometer 55 and subject the light to photoelectric conversion. The PDs 56R, 56G, 56B then output analog pixel signals, which the corresponding ADCs 57R, 57G, 57B sample at predetermined timings, convert to digital pixel signals, and output to the image processor 45.

While the scanning endoscope 100 is connected to the observation apparatus body 40, the image processor 45 reads the scanning pattern information of the scanning endoscope 100 from the storage 108. The image processor 45 then stores the pixel signals for each color, obtained from the ADCs 57R, 57G, 57B during scanning of the object being observed 70, at rendering positions of a frame memory in correspondence with the time points in the scanning pattern information read from the storage 108. The image processor 45 thus calibrates the pixel positions of pixel signals of each color obtained from the ADCs 57R, 57G, 57B by referring to the scanning pattern information read from the storage 108 and stores the pixel positions at the corresponding rendering positions in the frame memory. The image processor 45 performs necessary image processing, such as interpolation, during or after the completion of scanning of each frame, generates images of sequential frames of the object being observed 70, and displays the images on the display 60.

The storage 46 stores information such as control programs of the observation apparatus body 40. The storage 46 may also function as a working memory for the image processor 45.

FIG. 8 is a flowchart illustrating the main processing of image calibration operations performed by the endoscopic observation apparatus 30 in FIG. 7. First, the controller 41 drives the light source 42 and the drive controller 43 drives the actuator 103 of the scanning endoscope 100 to start scanning of the object being observed 70 with illumination light (step S801).

Next, during scanning of the object being observed 70, the controller 41 uses the optical detector 44 to sample analog pixel signals, output from the PDs 56R, 56G, 56B, with the ADCs 57R, 57G, 57B at a sequential predetermined plurality of time points $t_k$ (k=0, 1, ..., n) from the start of scanning to acquire digital pixel signals (step S802).

Subsequently, the controller 41 uses the image processor 45 to perform image calibration by storing pixel signals of each color obtained from the ADCs 57R, 57G, 57B at rendering positions of the frame memory in correspondence with the time points in the scanning pattern information read from the storage 108 (step S803). The controller 41 then uses the image processor 45 to perform necessary image processing, such as interpolation, based on the calibrated pixel signals at the rendering positions, to generate an image of the object being observed 70 and to display the image on the display 60 (step S804).

In the flowchart in FIG. 8, steps S801 and S802 correspond to the step of generating the pixel signals, and step S803 corresponds to a step of arranging the pixel signals. Processing that includes steps S801 to S803 corresponds to a step of generating a display image.

The endoscopic observation apparatus 30 according to this embodiment thus calibrates the pixel positions of the object being observed 70 using the scanning pattern information measured through the screen as the scanning pattern information of the scanning endoscope 100 in use. This configuration allows highly accurate image calibration and yields a high quality observation image.

This disclosure is not limited to the above embodiments, and a variety of changes or modifications may be made. For example, in Embodiment 5, the observation apparatus body 40 may include the functions of the measurement apparatus body 10 in FIG. 1, and as described in Embodiments 1 to 4, before scanning the object being observed 70, the PSD 12 may be connected, and the observation apparatus body 40 may measure the scanning pattern of the scanning endoscope 100 through the screen 11, subsequently calibrate the scanning image of the object being observed 70, and display the image. In this case, the measured scanning pattern information may be stored in the storage 46 of the observation apparatus body 40, and the storage 108 of the scanning endoscope 100 may be omitted. Also, the scanning pattern information may be measured as above for various types of scanning endoscopes 100, and the various pieces of scanning pattern information may each be stored along with identification information on the corresponding scanning endoscope 100 in the storage 46 of the observation apparatus body 40, and the identification information of a scanning endoscope 100 may be stored in the storage 108 of the scanning endoscope 100. The scanning pattern information for the identification information corresponding to the scanning endoscope 100 connected to the observation apparatus body 40 may then be read, and image calibration of the object being observed 70 may be performed.

If the time points at which the position of the irradiation spot (coordinate information) is acquired are the same as the time points at which the pixel signals of the object being observed 70 are acquired, the scanning pattern information may be chronological coordinate information, omitting the time information. The image of the object being observed 70 may be calibrated by temporarily storing the scanning image of the object being observed 70 in memory and then rearranging the pixel positions based on the scanning pattern information.

In FIG. 1, a portion or the entirety of the drive controller 18, calculator 19, and storage 20 may be included in the controller 16. Similarly, in FIG. 7, a portion or the entirety of the drive controller 43, the optical detector 44, the image processor 45, and the storage 46 may be included in the controller 41. The actuator 103 of the scanning endoscope 100 is not limited to a piezoelectric method and may instead adopt another known driving method, such as a MEMS mirror or an electromagnetic method that uses coils and a permanent magnet. In Embodiment 5, the case of scanning by simultaneously irradiating light of the colors R, G, B on the object being observed 70 has been described. Alternatively, light of each color may be irradiated and images displayed by a frame sequential method, or light of each color may be irradiated sequentially within one scan, with an image then being displayed. Furthermore, this disclosure is not limited to an endoscopic observation apparatus and may also be adopted in a scanning microscope.

REFERENCE SIGNS LIST

10 Measurement apparatus body
11 Screen
12 PSD (optical position detector)
16 Controller
17 Light source
18 Drive controller
19 Calculator
20 Storage
21 Projection optical system
22 Beam splitter
23 Image forming optical system
24 Imager
30 Endoscopic observation apparatus
40 Observation apparatus body
41 Controller
42 Light source
43 Drive controller
44 Optical detector
45 Image processor
46 Storage
100 Scanning endoscope
101 Optical fiber for illumination
102 Optical fibers for receiving light
103 Actuator
104 Illumination optical system
108 Storage

The invention claimed is:

1. An apparatus for calibrating an optical scanning apparatus that scans an object being illuminated with illumination light and generates a display image of the object being illuminated, the apparatus comprising:

a screen arranged to be scanned by the illumination light;

an optical position detector configured to detect irradiation spots of the illumination light on the screen;

a projection optical system configured to project the irradiation spots on the screen onto the optical position detector; and a processor configured to sequentially detect positions of the irradiation spots at a predetermined plurality of time points to measure a scanning pattern of the illumination light.

2. The apparatus according to claim 1, wherein the screen has a thickness equal to or less than a diameter of one of the irradiation spots.

3. The apparatus according to claim 1, wherein at least one of a first condition, a second condition, and a third condition is satisfied:

the first condition being that the screen has a thickness equal to or less than a diameter of one of the irradiation spots;

the second condition being that a diffusion angle of the illumination light by the screen is equal to or greater than a scanning angle of view; and the third condition being that a numerical aperture of the projection optical system on the screen side is 0.2 or greater.

4. The apparatus according to claim 1, further comprising a storage configured to store the measured scanning pattern of the illumination light.

5. The apparatus according to claim 1, further comprising an image sensor configured to image the screen and acquire an image of the scanning pattern of the illumination light.

* * * * *